(12) United States Patent
Ein-Gal

(10) Patent No.: US 7,349,730 B2
(45) Date of Patent: Mar. 25, 2008

(54) RADIATION MODULATOR POSITIONER

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 430 days.

(21) Appl. No.: 11/031,997

(22) Filed: Jan. 11, 2005

(65) Prior Publication Data

US 2006/0173294 A1    Aug. 3, 2006

(51) Int. Cl.
*A61N 5/00* (2006.01)
*A61B 6/00* (2006.01)

(52) U.S. Cl. .......................... 600/427; 376/68

(58) Field of Classification Search ................ 600/426, 600/414, 410, 427; 378/68, 196, 55
See application file for complete search history.

(56) References Cited

U.S. PATENT DOCUMENTS

| | | | |
|---|---|---|---|
| 5,299,254 A * | 3/1994 | Dancer et al. ............... | 378/163 |
| 5,572,568 A * | 11/1996 | Kanemitsu .................. | 378/206 |
| 5,745,545 A * | 4/1998 | Hughes ........................ | 378/65 |
| 5,769,861 A * | 6/1998 | Vilsmeier .................... | 606/130 |
| 6,035,228 A * | 3/2000 | Yanof et al. ................. | 600/429 |
| 6,275,564 B1 * | 8/2001 | Ein-Gal ........................ | 378/68 |
| 6,631,284 B2 * | 10/2003 | Nutt et al. ................... | 600/427 |
| 6,694,169 B2 * | 2/2004 | Kennedy et al. ............. | 600/426 |
| 6,847,838 B1 * | 1/2005 | Macey et al. ................ | 600/431 |
| 7,014,361 B1 * | 3/2006 | Ein-Gal ....................... | 378/197 |
| 2002/0115932 A1 * | 8/2002 | Kennedy et al. ............. | 600/424 |
| 2003/0004405 A1 * | 1/2003 | Townsend et al. ........... | 600/407 |
| 2003/0212320 A1 * | 11/2003 | Wilk et al. ................... | 600/407 |
| 2004/0133101 A1 * | 7/2004 | Mate et al. .................. | 600/426 |
| 2005/0261570 A1 * | 11/2005 | Mate et al. .................. | 600/411 |

\* cited by examiner

*Primary Examiner*—Eric Winakur
*Assistant Examiner*—Helene Bor
(74) *Attorney, Agent, or Firm*—Dekel Patent Ltd.; David Klein

(57) ABSTRACT

A radiation modulator positioner operative to cause a relative motion between a radiation modulator and a radiation source housing, wherein said radiation source housing and said radiation modulator positioner are detached and free to move relative to each other in at least one degree of freedom.

11 Claims, 3 Drawing Sheets

RADIATION MODULATOR POSITIONER

FIELD OF THE INVENTION

This invention relates generally to systems with radiation sources (e.g., a Cobalt teletherapy unit or a linear accelerator for radiation therapy) and/or radiation modulators (e.g., collimators and physical compensators) that modulate a radiation beam. Such systems are used, for example, for radiotherapy and radiosurgery, and may employ techniques such as Intensity Modulated Arc Therapy (IMAT), Intensity Modulated Radiotherapy (IMRT), stereotactic radiosurgery and fractionated radiotherapy. The invention relates particularly to such a system wherein the radiation modulator and the radiation source housing may be positioned independently of each other, and may be used in conjunction with an imaging system for target localization for performing Image-Guided Radiation Therapy (IGRT).

BACKGROUND OF THE INVENTION

As is well known in the art, many radiotherapy and radiosurgery systems employ radiation sources for producing radiation beams, and radiation modulators (e.g., collimators, attenuating blocks and physical compensators) for defining radiation beam characteristics such as beam shape and/or beam intensity profiles. Such beams are used for imaging or treatment. Radiation modulators are either rigidly integrated with the radiation source housing or are detachable units capable of being on-demand attached to the radiation source housing.

When in use, a detachable beam modulator and a radiation source housing are rigidly attached to each other, such that not a single degree of freedom is available for a relative displacement between the two. Albeit leaves of a multi-leaves collimator are adapted to move, a detachable multi-leaves collimator system is also rigidly attached to the radiation source housing.

As is also well known in the art, radiation-imaging systems are used for target localization. For example, kilo-volt x-ray systems incorporate x-ray sources and associated detectors, and portal imaging systems use megavolt radiation sources for treatment and imaging. Such imaging systems are either integrated with the radiation source housing or are separate stationary units, generally ceiling and floor mounted dual units, since target localization requires imaging from two orientations. Once target position is determined, a sophisticated treatment couch (incorporating up to six motion-related degrees of freedom) moves the patient to the desired position.

Industry leaders currently offer systems where a radiation source, a multileaf collimator and imaging devices are integrated into one unit, operating in conjunction with a sophisticated treatment couch. Such units may be used for Image-Guided Radiation Therapy (IGRT) for the purpose of improved treatment due to improved target localization in real-time. For example, Siemens Medical Solutions manufactures the PRIMATOM System. This is a multifunctional hybrid configuration, consisting of a Siemens PRIMUS Linear Accelerator and a Siemens SOMATOM CT scanner with Sliding Gantry. The PRIMATOM System is intended to combine image guidance with radiation treatment delivery, with the aim of providing accurate, near real-time target localization within the treatment room. The oncologist is provided with current information on the size, shape and location of the target volume and nearby critical organs. Since the patient is in a ready-for-treatment position during CT acquisition, the information can be applied immediately for improved treatment accuracy.

IGRT may provide fast, 3-D tumor localization prior to irradiation, thereby providing the ability to accurately deliver escalated doses, reduce complications, and evaluate therapeutic effectiveness of treatment. X-ray or ultrasonic diagnostic imaging in the treatment room may provide diagnostic quality images with the patient in the actual treatment position, and may help indicate anatomical movement of the patient during treatment.

However, the prior art systems with integrated radiation source, collimators and imaging devices, in conjunction with a sophisticated treatment couch, are expensive, cumbersome and not easily adapted to units already in use.

SUMMARY OF THE INVENTION

The present invention seeks to provide a novel positioner for a radiation modulator and radiation system, as is described more in detail hereinbelow. The radiation modulator may include, without limitation, a collimator, a physical modulator or compensator, beam intensity modulation filter or other devices for shaping and/or modifying a radiation beam.

In accordance with one non-limiting embodiment of the invention, a separate positioner may be used for mechanically positioning the radiation modulator relative to the radiation beam(s). A positioner that is separate and detached from a radiation producing device, such as a Linear Accelerator (LINAC) or a cobalt machine, provides upgradeability and utilization flexibility. For example, the positioner may be transported to several locations or may be employed in several radiation-producing devices at the same location. The modulator positioner may be integrated into an Image-Guided Radiation Therapy (IGRT) system.

There is thus provided in accordance with an embodiment of the present invention apparatus including a radiation modulator positioner operative to cause a relative motion between a radiation modulator and a radiation source housing, wherein said radiation source housing and said radiation modulator positioner are detached and free to move relative to each other in at least one degree of freedom.

In accordance with an embodiment of the present invention a position sensor may sense a relative position of the radiation modulator and the radiation source housing, or a relative position of the radiation modulator positioner and a target. A controller may be in operative communication with the position sensor and operative to cause relative motion between the radiation modulator and the radiation source housing or target in accordance with information received from the position sensor.

The radiation modulator positioner may include a radiation modulator gantry rotatable about a radiation modulator gantry rotation axis, wherein the radiation modulator gantry rotation axis is adapted to be generally collinear with a rotation axis of the radiation source housing.

Alternatively, the radiation modulator positioner may include a radiation modulator gantry rotatable about two rotation axes whereas the rotation axes generally intersect at a common rotation center, and wherein the common rotation center is adapted to generally coincide with the radiation source.

The radiation modulator positioner may be free to move relative to the radiation source housing in a plurality of degrees of freedom, and may be mechanically constrained to move closely to the radiation source housing.

Further in accordance with an embodiment of the present invention imaging equipment may be provided to capture and process images of a target or of objects that are geometrically related to the target. The imaging equipment may be in operative communication with the radiation modulator controller and/or driver to cause positioning of radiation modulator relative to target. The imaging equipment may include an image detector alignable with the radiation modulator, and/or an imaging beam source and an image detector alignable with the imaging beam source. Fiducial markers may be attached to the radiation source housing and/or the radiation modulator and/or the target in order to provide—via imaging—positioning information of the target, the radiation source housing and the radiation modulator relative to each other.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1A:
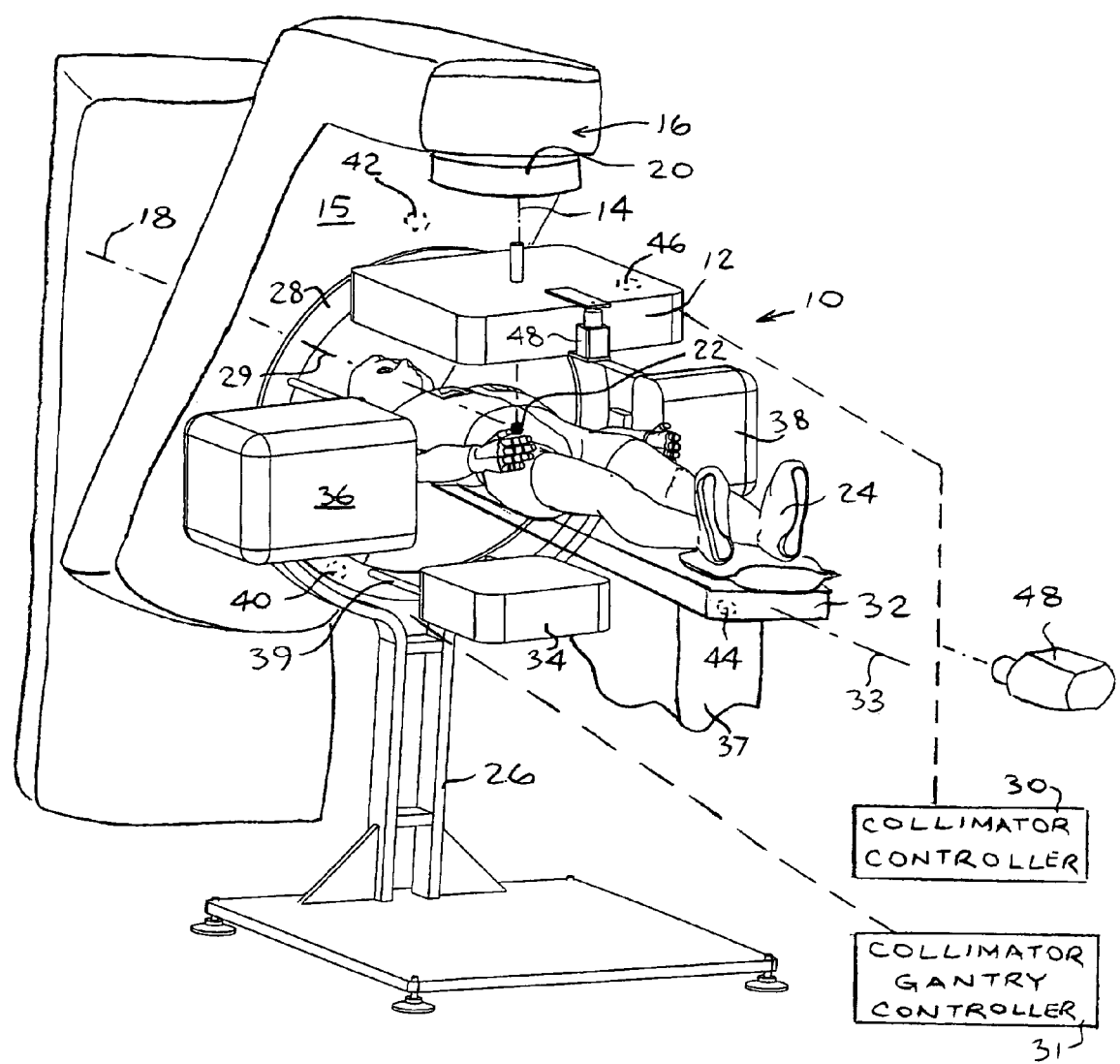
FIGS. 1A and 1B are simplified pictorial illustrations of a radiation modulator positioner, constructed and operative in accordance with an embodiment of the present invention.
Figure 1B:
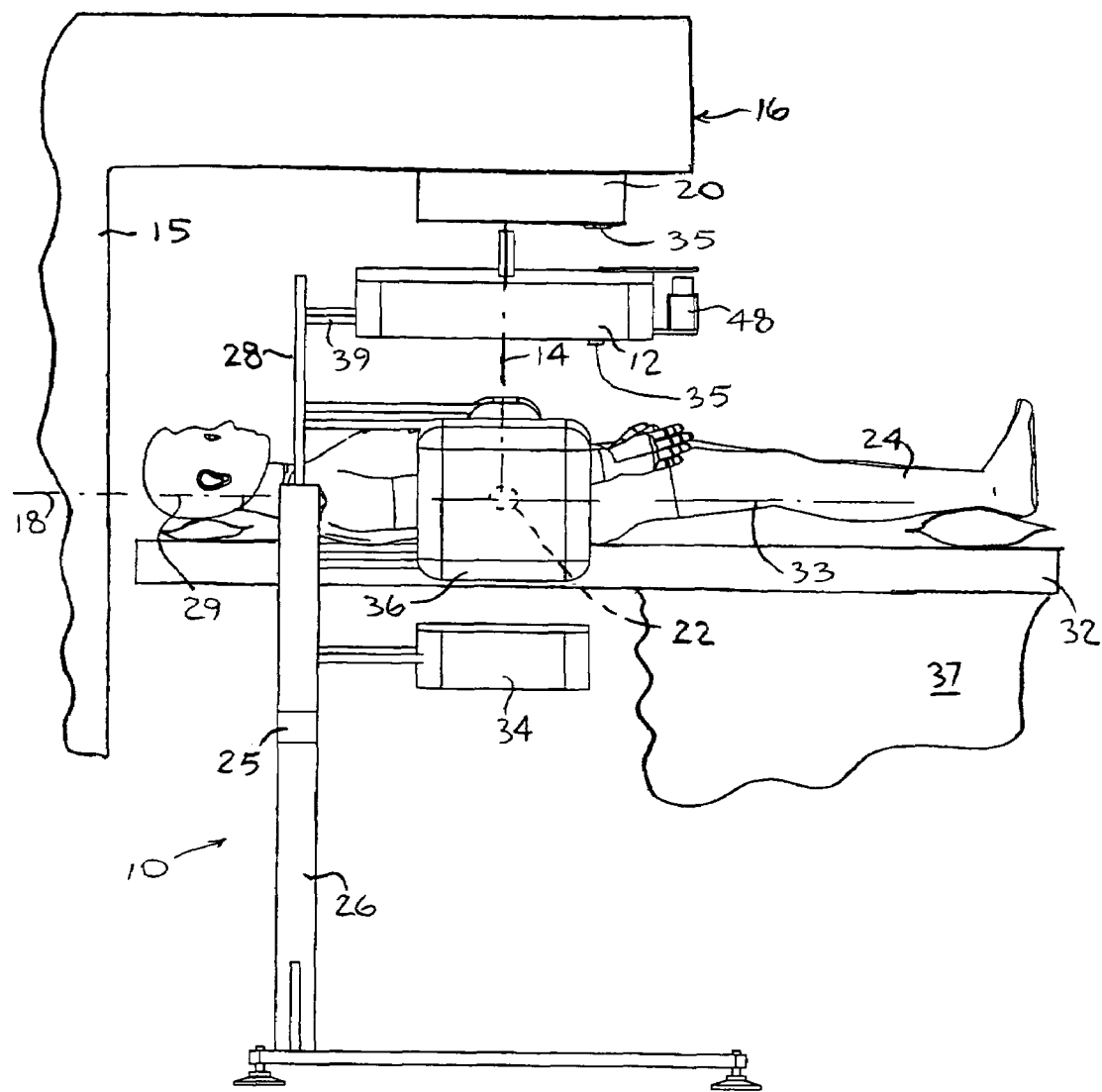

Reference is now made to FIGS. 1A and 1B, which illustrates a radiation modulator positioner 10, constructed and operative in accordance with an embodiment of the present invention.

The radiation modulator positioner 10 may be used to position one or more radiation modulators 12 for modulating a radiation beam 14 emanating from a radiation beam delivery device 16, such as a gantry 15 of an irradiation device (e.g., a LINAC system). Radiation beam delivery device 16 is positionable in a plurality of spatial orientations. For example, gantry 15 of radiation beam delivery device 16 may be rotated about a rotational axis 18, such as by means of an electrical, hydraulic or pneumatic driver and the like. A treatment head 20, also referred to herein as the radiation source housing 20 or simply the radiation source 20, may be part of or fastened to a portion of radiation beam delivery device 16, containing a source of radiation for producing radiation beam 14, such as but not limited to, electron, photon or any other radiation used in therapy. An object of the treatment plan is to direct the radiation beam 14 on a target 22 of an object 24, for example, a patient who is to be treated (referred to as patient 24).

The radiation modulator positioner 10 may include a chassis 26 (preferably stationary) and a radiation modulator gantry 28 movably mounted on chassis 26. Radiation modulator gantry 28 may be rotated about a radiation modulator gantry rotation axis 29, such as by means of an electric, hydraulic or pneumatic driver 25 (FIG. 1B) and the like. Radiation modulator 12 may be mounted on the movable radiation modulator gantry 28. Radiation modulator 12 may be any kind of radiation modulator suitable for modulating radiation beam 14, such as but not limited to, a collimator, a physical modulator or compensator, or beam intensity modulation filter or other devices for shaping and/or modifying a radiation beam. For example, radiation modulator 12 may include a multileaf collimator. As is known in the art, multileaf collimators include a plurality of radiation blocking leaves. It is emphasized that the term "leaves" is not limited to leaf-like structure, rather the term "leaves" encompasses any kind of radiation blocking structure, such as but not limited to, rods, plates, and the like, of any size and shape. Of course, the invention is not limited to multileaf collimators and the invention may be carried out with other kinds of collimators, such as but not limited to, (stationary) collimators like cones, attenuating blocks or other physical compensators. These may be mounted on the radiation modulator gantry 28 in stages in order to provide adequate relative radiation modulator/gantry motion.

The movement of the radiation blocking elements (also referred to herein as "leaves") of the radiation modulator may be controlled by a radiation modulator controller 30, which does not have to be mounted on the radiation modulator gantry 28. Such radiation modulator controllers are well known in the art, and may employ software to control movement of the collimator leaves, tailored to suit a treatment modality. The rotational movement of the radiation modulator gantry 28 may be controlled by a radiation modulator gantry controller 31, such as but not limited to, a servomotor working with position sensors in a closed loop control system. The radiation modulator controller 30 and the radiation modulator gantry controller 31 may be incorporated in one controller unit. The controllers 30 and 31 may be radiation-shielded if placed in the treatment room.

A treatment table 32 may be provided for the patient 24 to lie thereupon. The treatment table 32 may be positioned so that a portion of the patient 24 is exposed to radiation beam 14 modulated by radiation modulator 12. The treatment table 32 may be provided with a driver 37 in operative communication with any of the controllers for moving table 32. Driver 37 may be capable of moving and fine-tuning the position of the radiation modulator 12 and/or of the treatment table 32 (in the former case, driver 37 is a radiation modulator positioner, and in the latter case, driver 37 is a target positioner), so that the radiation modulator 12 is aligned with the radiation beam 14 and with the target 22.

An image detector 34 may be placed on the side of the patient 24 opposite the radiation modulator 12 for imaging the target zone. The target 22 and other portions of the patient 24 may be alternatively imaged by an imaging system, which may include an imaging beam source 36 (e.g., x-ray in the kilovolt range) and an image detector unit 38 placed on the opposite side of the patient 24. The imaging equipment may be used, for example, for localization of the target 22 relative to beam 14 and to radiation modulator 12. Fiducial markers 35 (FIG. 1B) may be attached to radiation source housing 20 and/or radiation modulator 12 and/or target 22 for providing registration data obtained by imaging the fiducial markers 35. As another example, an x-ray imaging system may compare projection images to prior CT (computer tomography) images for target localization. In one non-limiting embodiment of the invention, the radiation modulator gantry 28 may comprise a rotating ring, and the radiation modulator(s) 12 and the imaging equipment modules (e.g., image detector 34, imaging beam source 36 and image detector unit 38) may be mounted on arms 39 (FIG. 1B) at selected interfaces on the ring. Various sensors may be provided for sensing the position of different components of the system, such as but not limited to, a radiation modulator gantry position sensor 40 (e.g., for sensing the rotational position of the radiation modulator gantry 28), an irradiation gantry position sensor 42 (e.g., for sensing the rotational position of the gantry 15 of radiation beam delivery device 16 about rotational axis 18), and a table position sensor 44 (e.g., for sensing the position of the treatment table 32).

The radiation modulator 12 may be adjustably mounted on arm 39. The radiation modulator 12 may be moved with respect to the radiation modulator gantry 28, such as by means of a servomotor, which may be controlled by controller 30 or some other controller. A radiation modulator position sensor 46 may be provided for sensing the position of the radiation modulator 12. One or more viewing devices 48 (e.g., CCD or video cameras) may be provided at various locations in the treatment room (attached to walls, ceilings or other suitable structure) for monitoring the relative positions of the table 32, radiation modulator gantry 28, radiation modulator 12, and gantry 15 of radiation beam delivery device 16. For example, a viewing device 48 may be mounted on the housing of radiation modulator 12 for viewing markers on the radiation beam delivery device 16 and/or its treatment head 20, in order to sense the movement of the gantry 15 and cause the controllers to move the radiation modulator gantry 28 to keep radiation modulator 12 in alignment with radiation beam 14.

In general, the position sensors may comprise, without limitation, accelerometers, proximity sensors, encoders, CT scanners, x-ray fluoroscopes, ultrasound scanners, portal imagers and viewing devices, such as CCTV or CCD cameras, and many others. The position sensors may sense a spatial position of the radiation modulator 12, radiation modulator gantry 28, the radiation beam 14, the target 22, the table 32, the gantry 15, the radiation source housing 20, and/or the patient 24.

Since the radiation modulator 12 is not rigidly attached to the radiation source housing, the respective rotation axes, radii and centers do not perfectly coincide and the radiation modulator position relative to the radiation source varies. The following is one non-limiting example of steps for aligning the radiation modulator 12 with the radiation beam delivery device 16 for delivering the radiation beam 14 to the isocenter at the target 22. Initially, the treatment table 32 may be manually aligned with the rotation axis 18 of the gantry 15 of radiation beam delivery device 16. The manual alignment may be fine-tuned by feedback from viewing devices 48. The radiation modulator gantry 28 may be rotated about axis 29 to align radiation modulator 12 with the beam axis of radiation beam 14. Images obtained from the imaging equipment (e.g., image intensifier 34, imaging beam source 36 and image intensifier unit 38) may be used to verify and make fine adjustments to align radiation modulator 12 with the beam axis of radiation beam 14, as well as positional information obtained from viewing devices 48. Radiation modulator 12 may be moved independently of the radiation modulator gantry 28, if needed, for fine adjustments. Another fine adjustment may be provided by the radiation modulator controller 30, which may move the radiation modulator leaves so that the target 22 is aligned precisely with the radiation beam 14.

Thus, in one mode of operation, the gantry 15, along with the radiation source in the radiation beam delivery device 16, rotates about rotational axis 18 in accordance with a treatment modality. The rotational movement of the gantry 15 is sensed by the controllers, which command the radiation modulator gantry 28 to rotate about its rotational axis 29 in synchronization with the gantry 15, such that the radiation modulator 12 always remains aligned with the radiation beam 14. The position sensors and viewing devices may measure any discrepancy between the rotational movements of the radiation modulator gantry 28 and the gantry 15 of radiation beam delivery device 16, and the discrepancy may be corrected by moving any one of or combination of the radiation modulator gantry 28, the radiation modulator 12, the radiation modulator leaves, or the table 32, in a closed control loop, as mentioned previously.

Although the invention may be carried out without any connection or contact between the radiation modulator 12 and the radiation source housing 20, other methods for assisting the radiation modulator 12 to follow the motion of the gantry 15 may be employed, which may involve some contact interface therebetween.

Figure 2:
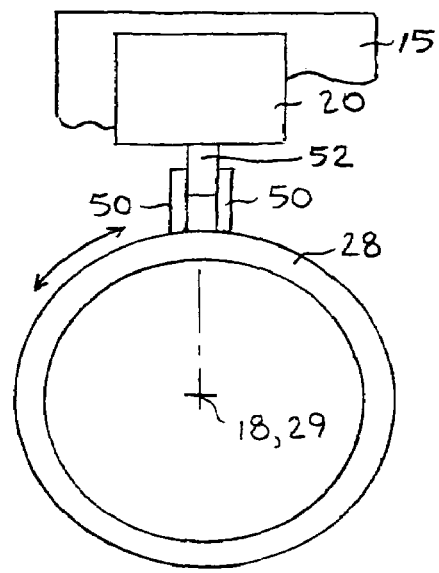
FIG. 2 is a simplified illustration of an optional interface between the radiation modulator positioner and a radiation source of a radiation beam delivery device, in accordance with an embodiment of the present invention.

Reference is now made to FIG. 2. For example, two parallel planar walls 50, perpendicular to the gantry motion (rotation about axis 29) may be attached to the radiation modulator gantry 28 and may interface and cooperate with a contact member 52 protruding from the radiation source housing 20. (Alternatively, the walls may be on the radiation source housing 20 and the contact member 52 may be on the radiation modulator gantry 28. Of course, other interfaces may also be employed.) Contact member 52 may be placed at close proximity to and between walls 50 (e.g., zero spacing, i.e., a snug press fit). As the gantry 15 rotates about its rotational axis 18, the contact member 52 may apply a force to the walls 50, which causes the radiation modulator gantry 28 to rotate in synchronization with gantry 15. Any measured shift in the position of the contact member 52 on the walls 50 may be used to control the motion of the radiation modulator 12 relative to the gantry 15 and, indirectly, to the radiation source. Of course, as described above, the position sensors and viewing devices may still be used for fine adjustments, as well as moving the radiation modulator 12 and its leaves.

In general, the radiation modulator 12 may move with respect to the radiation source 20 in at least one degree of freedom, called the detached degree of freedom. The at least one detached degree of freedom may be measured and corrected, as described hereinabove, such as with the position sensors, controllers, drivers, and movement of the radiation modulator itself and/or its radiation leaves. For example, radiation modulator 12 may be attached to the radiation source 20 with respect to one or more degrees of freedom and may be detached with respect to the radiation source 20 in a plurality of "detached" degrees of freedom.

The term "detached" degree of freedom means that the radiation modulator 12 is not at all connected to the radiation source housing 20 in that degree of freedom. This should not be confused with the situation in some prior art radiation modulators which have a set of modulating apertures and the radiation modulator can be rotated about an axis parallel to the beam axis to bring one of the modulating apertures in alignment with the beam axis. In those prior art systems, the radiation modulator itself is rigidly attached to the radiation source housing and is never detached therefrom. In contrast, in the present invention, the radiation modulator 12 is detached from the radiation source housing 20 in at least one degree of freedom.

Figure 3:
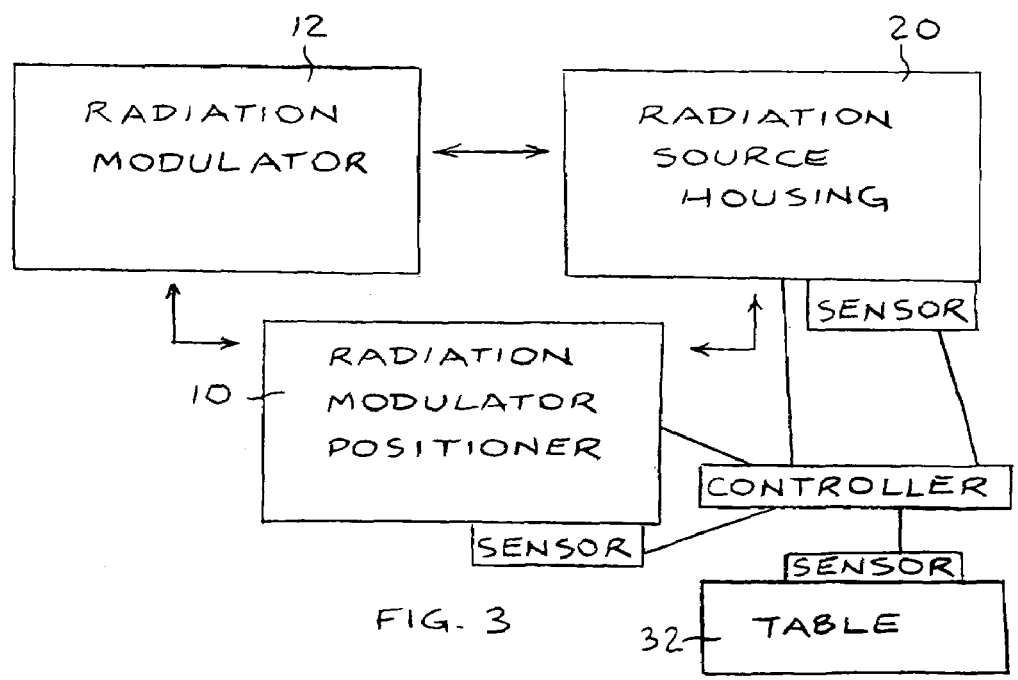
FIG. 3 is a simplified block diagram that summarizes features of embodiments of the present invention.

Reference is now made to FIG. 3, which in block diagram form, summarizes features of embodiments described hereinabove.

Radiation modulator positioner 10 may cause relative motion between radiation modulator 12 and radiation source housing 20. This means that radiation modulator positioner 10 may cause radiation modulator 12 to move with respect to radiation source housing 20, which remains stationary, or alternatively, radiation modulator positioner 10 may cause radiation source housing 20 to move with respect to radiation modulator 12, which remains stationary. Radiation modulator positioner 10 is not rigidly connected to radiation source housing 20 and/or radiation modulator 12, such that radiation source housing 20 and radiation modulator positioner 10 are free to move relative to each other in at least one degree of freedom. One or more position sensors (described above) may sense the relative position of radiation modulator positioner 10 and radiation source housing 20. A controller (e.g., controller 31 and/or driver 37) may operative with the position sensor(s) and radiation modulator positioner 10 to cause relative motion between radiation modulator 12 and radiation source housing 20 in accordance with information received from the position sensor(s).

As another possibility, once the relative position of the radiation source housing 20 and the radiation modulator 12 is sensed, the controller may cooperate with table position sensor 44 and move the target relative to modulator 12 (and/or source housing 20).

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. Apparatus comprising:
   a radiation modulator positioner operative to cause a relative motion between a radiation modulator and a radiation source housing, wherein said radiation source housing and said radiation modulator positioner are detached and free to move relative to each other in at least one degree of freedom;
   an imaging system adapted to capture position-related images of at least one of a target and a fiducial mark, wherein said imaging system is aligned with said radiation modulation positioner; and
   an imaging processer adapted to process said position-related images and derive information about a relative position of said radiation modulator positioner to at least one of said radiation source housing and the target, wherein said radiation modulator and at least a portion of said imaging system are mounted on arms of a rotating ring at selected interfaces on said rotating ring.

2. The apparatus according to claim 1, further comprising a position sensor adapted to sense a relative position of said radiation modulator positioner and said radiation source housing, and a controller in operative communication with said position sensor and operative to cause relative motion between said radiation modulator and said radiation source housing in accordance with information received from said position sensor.

3. The apparatus according to claim 1, further comprising a position sensor adapted to sense a relative position of said radiation modulator positioner and a target, and a controller in operative communication with said position sensor and operative to cause relative motion between said radiation modulator positioner and said target in accordance with information received from said position sensor.

4. The apparatus according to claim 1, wherein said radiation modulator positioner comprises a radiation modulator gantry rotatable about a radiation modulator gantry rotation axis, wherein said radiation modulator gantry rotation axis is adapted to be generally collinear with a rotation axis of said radiation source housing.

5. The apparatus according to claim 1, wherein said radiation modulator positioner comprises a radiation modulator gantry rotatable about two rotation axes whereas said rotation axes generally intersect at a common rotation center, and wherein said common rotation center is adapted to generally coincide with said radiation source.

6. The apparatus according to claim 1 whereas said radiation modulator positioner is free to move relative to the radiation source housing in a plurality of degrees of freedom, and is mechanically constrained to move closely to the radiation source housing.

7. The apparatus according to claim 1, wherein said radiation source housing includes a radiation source operable to produce a radiation beam.

8. The apparatus according to claim 7, wherein said radiation modulator adapted to modulate a radiation beam emanating from said radiation source housing.

9. The apparatus according to claim 1, wherein said rotating ring of said radiation modulator positioner comprises a radiation source gantry rotatable about a radiation source gantry rotation axis, wherein said radiation source gantry rotation axis generally intersects a target to be irradiated.

10. The apparatus according to claim 1, wherein said rotating ring of said radiation modulator positioner comprises a radiation source gantry rotatable about at least two rotation axes whereas said rotation axes generally intersect at a common rotation center, and wherein said common rotation center is adapted to generally coincide with a target.

11. The apparatus according to claim 1, further comprising a treatment table adapted for a patient to lie thereupon, said treatment table being positioned so that a portion of the patient is exposed to a radiation beam emanating from said radiation source housing and modulated by said radiation modulator, and further comprising a driver adapted to adjust positions of at least one of said radiation modulator and said treatment table so that said radiation modulator is aligned with the radiation beam and with a target.

* * * * *